United States Patent [19]
Spitz et al.

[11] Patent Number: 5,746,693
[45] Date of Patent: May 5, 1998

[54] FLEXIBLE ENDOSCOPIC APPARATUS AND METHODS OF USE

[75] Inventors: Aaron Spitz, 1249 9th St. #6, Santa Monica, Calif. 90401; Perry Sutaria, 445 E. 68th St. #8E, New York, N.Y. 10021

[73] Assignees: Aaron Spitz, Santa Monica, Calif.; Perry Sutaria, New York, N.Y.

[21] Appl. No.: 446,296

[22] Filed: May 22, 1995

[51] Int. Cl.$^6$ ............................................. A61B 1/04
[52] U.S. Cl. ........................ 600/112; 600/160; 600/162
[58] Field of Search ........................ 600/160, 162, 600/164, 165, 163, 172, 174, 102, 103, 137, 138, 178, 197, 245, 248, 112, 113; 385/117; 359/503, 506; 433/29, 31; 362/105, 804, 32; 354/62

[56] References Cited

U.S. PATENT DOCUMENTS

| | | |
|---|---|---|
| 3,830,230 | 8/1974 | Chester . |
| 4,265,561 | 5/1981 | Heckele . |
| 4,274,128 | 6/1981 | Malis . |
| 4,369,767 | 1/1983 | Shishido .................... 600/112 |
| 4,552,131 | 11/1985 | Omagari .................. 600/112 X |
| 4,565,423 | 1/1986 | Ueda ...................... 600/165 X |
| 4,601,284 | 7/1986 | Arakawa et al. ............... 600/112 |
| 4,621,618 | 11/1986 | Omagari .................. 600/165 X |
| 4,870,950 | 10/1989 | Kanbara et al. ............ 600/165 X |
| 4,967,323 | 10/1990 | Johnson et al. . |
| 5,039,198 | 8/1991 | Van Beek .................... 385/117 |
| 5,127,393 | 7/1992 | McFarlin et al. . |
| 5,156,141 | 10/1992 | Krebs et al. . |
| 5,359,992 | 11/1994 | Hori et al. ................. 354/62 X |

FOREIGN PATENT DOCUMENTS 1616597 12/1990 U.S.S.R. ........................... 600/162

Primary Examiner—Beverly M. Flanagan
Attorney, Agent, or Firm—Arnall Golden & Gregory, LLP

[57] ABSTRACT

An attachment for an endoscope is disclosed, the attachment comprising a flexible extension portion for extending an optical output of the endoscope eyepiece to a remote location for direct visualization at the remote location, a coupling for optically coupling one end of the flexible extension portion to the endoscope, and a mechanism for stably positioning a remote end of the flexible extension portion in front of an eye of a person at the remote location. The flexible extension portion will preferably include a receiving lens for receiving light from the endoscope eyepiece, an elongate, sheathed optical fiber having one end connected to the receiving lens, another eyepiece connected to the remote end of the optical fiber, and the optical fiber is of sufficient length and flexibility to permit the receiving lens to be freely rotated and manipulated while the remote eyepiece is stably positioned by the positioning mechanism.

22 Claims, 2 Drawing Sheets

FLEXIBLE ENDOSCOPIC APPARATUS AND METHODS OF USE

BACKGROUND OF THE INVENTION

1. Field of the Invention

The present invention pertains to a flexible endoscopic apparatus for medical examination procedures, and to methods of assembling and utilizing same. More particularly, the present invention pertains to a flexible endoscopic apparatus including a conventional endoscope or endoscopic probe together with a flexible extension which permits an output lens or eyepiece attached at a remote end of the extension to be conveniently supported by headgear worn by an examiner so that the examiner's head and torso may be comfortably positioned, and the examiner's hands remain free to extensively manipulate the endoscopic probe, during an examination procedure.

2. Description of Relevant Art

There are known endoscopic devices including features which facilitate their use during an examination procedure. For example, Heckele, U.S. Pat. No. 4,265,561, discloses a headband device to be worn by a person performing endoscopic examination which includes adjustable clamp means for receiving and clamping the eyepiece of an endoscope in front of the person's right or left eye. Although such patented holder eliminates the conventional necessity of hand-holding the endoscope eyepiece in front of an examiner's eye, it otherwise restricts and limits the type and degree of manipulations that the examiner can perform with the endoscope when its eyepiece is clamped by the holder. Such patented holder does not eliminate the conventional need for the examiner to keep his or her head in close proximity to his or her hands, as well as to the patient's body, in often awkward positions.

McFarlin et al., U.S. Pat. No. 5,127,393, discloses a endoscopic apparatus including a flexible endoscope usable in combination with a rigid introducer. The flexible endoscope includes a rigid hub with a plurality of flexible tubular members connected thereto for respectively providing light input to, light output from, and fluid input/output to the hub. The light output tubing is adapted to be connected to an eyepiece or to a video camera. Again, although the disclosed endoscopic apparatus provides some degree of convenience for use in an endoscopic examination, it is relatively complex, restricts some movements of the endoscope during an examination, and does not alleviate the conventional need for the examiners to awkwardly position their heads in close proximity to their hands and to the patients.

Krebs et al., U.S. Pat. No. 5,156,141, discloses a quick connect coupling for connecting an endoscope eyepiece to a video camera, and which permits the end of the endoscope to be rotated relative to the camera. When connected to the endoscope, the camera may, for example, be used to project the optical image from the eyepiece through a CRT monitor or the like disposed near the examiner so that theoretically the examiner can watch the image on the monitor, and whereby the examiner's head need not be awkwardly positioned closely to his or her hand and to the patient. As a practical matter, however, the image projected by the camera through the monitor is simply not as sharp and clear as the image viewed directly from the endoscope eyepiece. Correspondingly, many, if not most, examiners will often not use the camera and monitor despite their availability, and instead view an examination directly through the endoscope eyepiece for the better clarity and accuracy achieved thereby.

Chester, U.S. Pat. No. 3,830,230, and Malis, U.S. Pat. No. 4,274,128, disclose surgical headlamp devices mounted on headbands to be worn by surgeons during medical procedures, each of which includes a headband/harness, a lamp output lens fixed to a front portion of the headband in an adjustable manner, and a fiberoptic-type remote source of light connectable to the headlamp output lens. While all of these known headlamp devices are adequate for their intended purposes, the disclosed structures for supporting headlamps in stationary positions are not suitable for use with highly manipulated structures such as endoscopes.

SUMMARY OF THE INVENTION

The present invention has been developed to overcome the above-discussed limitations and disadvantages of known endoscopic apparatus, and to satisfy a need in the art for a simple, flexible endoscopic apparatus which may be conveniently and comfortably supported by an examiner during an examination without imposing any restrictions on the degree or type of movements through which the body examining probe of the apparatus may be manipulated during an examination procedure.

According to the invention there is provided an attachment for an endoscope having an eyepiece, comprising: flexible extension means for extending an optical output of an endoscope eyepiece to a remote location; coupling means for optically coupling one end of said flexible extension means to the endoscope eyepiece; and means for stably positioning a remote end of said flexible extension means in front of an eye of a person at the remote location. Preferably, the flexible extension means includes a receiving lens for receiving light output from the eyepiece, an elongate, sheathed optical fiber or fiber bundle having one end connected to said receiving lens, an output lens connected to the remote end of the optical fiber, and the sheathed optical fiber being of sufficient length and flexibility to permit the receiving lens to be freely rotated and manipulated while the output lens is stably positioned by the positioning means; and the coupling means includes a retainer for securing the receiving lens to the eyepiece. Also preferably, the positioning means will include an adjustable support band which selectively fits on a user's head, clamp means connected to the band selectively clamping the output lens to the band, means for adjusting a position of the clamp means (and hence the clamped output lens) relative to the support band, and means for securing an intermediate portion of said optical fiber over top and rear portions of the support band such that it does not interfere with the user's movements and manipulations of the endoscope during an examination procedure.

According to the invention there is also provided a flexible endoscopic apparatus comprising a light transmissive probe, either flexible or rigid, for being inserted within a body cavity; coupling means for selectively coupling the probe to a high intensity light source; the probe including a first lens for transmitting light from the light source to be output from a free end of the probe; a second lens for receiving in one end thereof light reflected into the free end of the probe and transmitting the reflected light through a sheathed optical fiber to an eyepiece; means for positioning the eyepiece in front of an eye of a user; and the sheathed optical fiber being sufficiently long and flexible, preferably 4–12 feet long, that the light transmissive probe may be freely rotated and manipulated (within a body cavity) while the eyepiece is maintained in a desired position by the positioning means.

It is an object of the invention to provide a flexible endoscopic apparatus, either as an attachment for a conventional endoscope or a self-sufficient endoscope, which greatly facilitates an examination procedure by permitting the body probing portion of the apparatus to be rotated and manipulated to a very large extent with only minimal restrictions, while an optical output or eyepiece of the apparatus is stably maintained in position in front of an examiner's eye at a relatively large distance from the probing portion, so that the examiner may be comfortably postured (in an upright sitting position, for example) during an examination and can otherwise conduct very thorough and dexterous examinations.

It is a further object of the invention to provide such a flexible endoscopic apparatus which provides the examiner with an optimally clear image of a probed body part.

It is another object of the invention to provide such a flexible endoscopic apparatus which is relatively simple in structure and inexpensive to manufacture.

It is still another object of the invention to provide such a flexible endoscopic apparatus which is easily adjustable for use by different persons and which is also suitable for use in substantially any endoscopic type examination, so that a single version/model of the apparatus may be economically produced in large quantities.

Other objects, advantages and salient features of the present invention will be apparent from the following detailed description, which when taken into conjunction with the annexed drawings discloses preferred embodiments of the present invention.

DETAILED DESCRIPTION OF THE PREFERRED EMBODIMENTS

Figure 1:
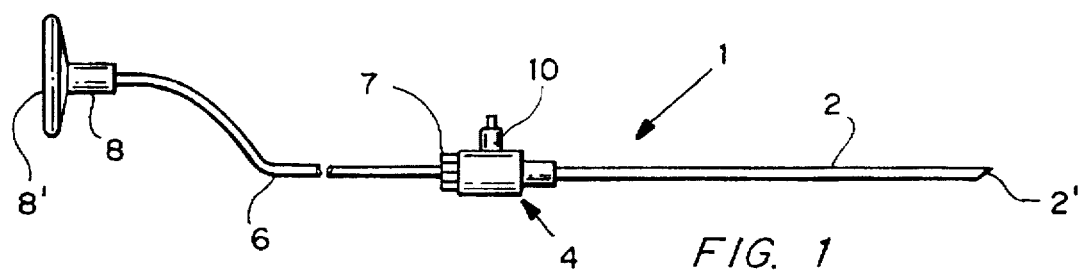
FIG. 1 is a side view of body probe and output portions of a flexible endoscopic apparatus according to a first preferred embodiment of the invention.
Figure 3:
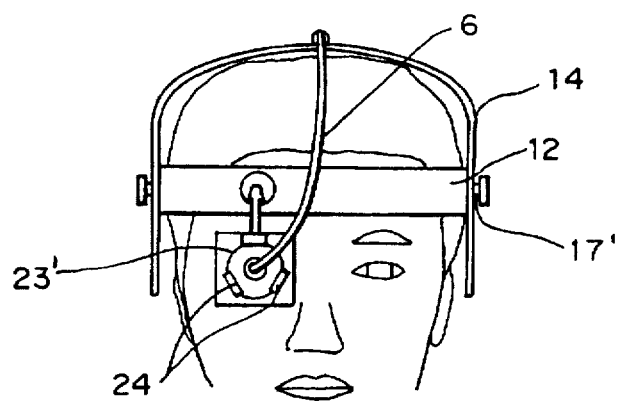
FIG. 3 is a front elevational view of an eyepiece positioning portion of the endoscopic apparatus according to any of the embodiments shown in FIGS. 1, 2, 5 and 6.
Figure 4:
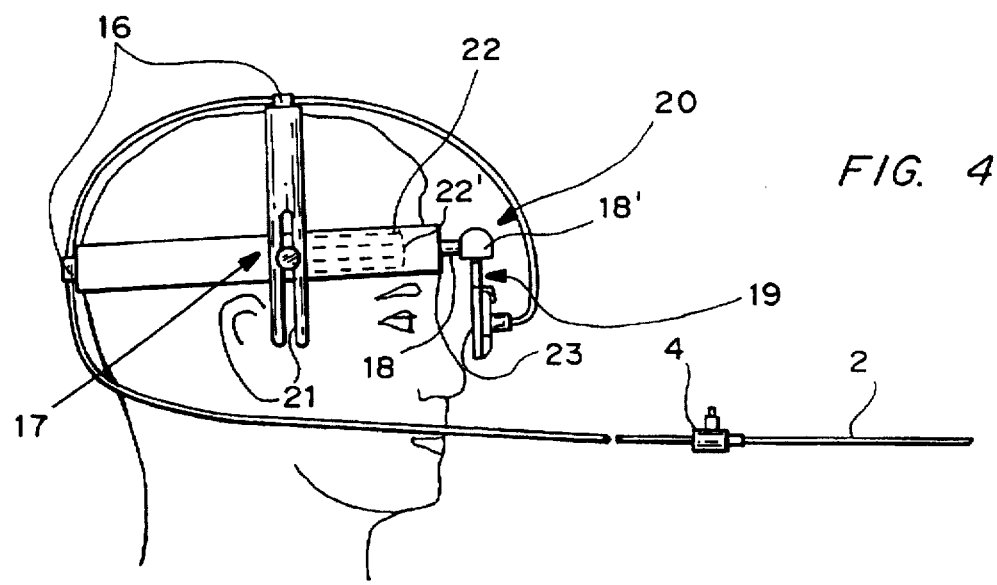
FIG. 4 is a side elevational view of the support portion of FIG. 3 together with the flexible endoscope of FIG. 1.

Referring to FIGS. 1, 3 and 4 there is shown a flexible endoscopic apparatus 1 according to a first preferred embodiment of the invention. As shown in FIG. 1, an endoscope or cystoscope portion of the apparatus includes a body cavity probe or telescope 2 of conventional design with a series of rigid, typically glass lenses and an outer protective sheath; an elongate, flexible optical fiber or fiber bundle (hereinafter "fiber") 6 having an outer, protective, flexible sheath; a coupling 4 for operatively joining a high intensity light source lead and other examination tools to the probe 2; and an eyepiece 8 joined to the opposite or remote end of the optical fiber 6.

The coupling 4 includes a fitting 10 to which a lead from a high intensity light source may be fitted for providing high intensity light to the probe 2. In the conventional probe structure, a first lens transmits the high intensity light and projects same from the output tip, while a second lens receives light reflected back into the tip and transmits the reflected light to the viewing eyepiece at the opposite end of the probe. According to the present invention, however, the second lens which receives light reflected back into output tip 2' is coupled to the flexible optical fiber 6, while the eyepiece 8 is disposed remotely from the probe at the opposite end of the flexible fiber 6. The coupling 4 will typically also have other ports/fittings thereon (not shown) to which a water source may be connected and through which a guidewire, catheter or other instrument may be passed. The probe sheath will also have openings defined therethrough for channeling the water and catheter to the probe tip 2'. Indicated at 7 is a focus adjustment knob which is preferably provided for adjusting the focus of an image output from the probe lens to the flexible optical fiber 6.

The lenses of the probe or telescope 2 of FIG. 1 may be rigid glass lenses as are conventionally used in rigid type endoscopes and cystoscopes. Alternatively, one or both of the lenses may be optical fibers or fiber bundles, and if the second lens is an optical fiber or fiber bundle, it may be formed integrally with the elongate fiber 6.

With reference to FIGS. 3 and 4, an eyepiece positioning portion of the apparatus includes bands 12 and 14 for being supported about a user's head, clips 16 for securing an intermediate portion of the optical fiber 6 to rear and upper portions of the bands 12 and 14, respectively, a support member 18 extending from a front portion of the band 12, an eyepiece mount 19 for securing the eyepiece 8, and a universal type pivot joint 20 interconnecting ends of the support member 18 and the eyepiece mount 19. The diameter of the band 12 and the relative height of the band 14 above the band 12 are adjustable through an adjustment means generally indicated at 17 so that the bands may be properly fitted to any size head.

Figure 2:
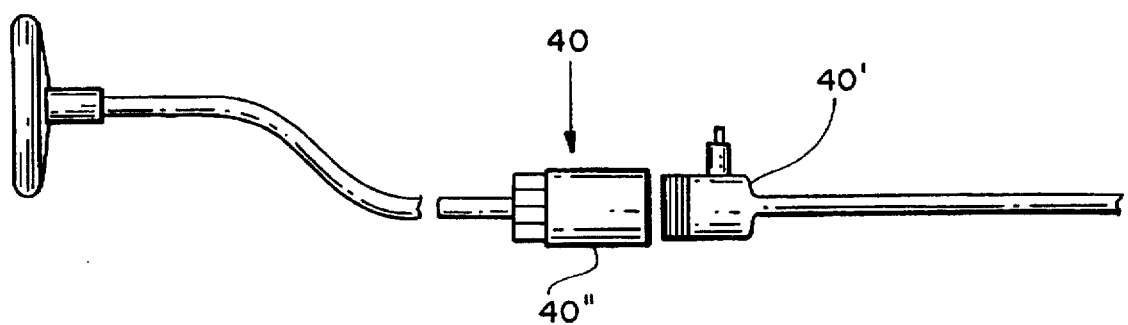
FIG. 2 is a slight modification of the preferred embodiment of FIG. 1.

Referring to FIG. 2, there is shown a flexible endoscopic apparatus similar to that of FIG. 1, but having a modified coupling 40 which joins the probe to the fiber 6 and to the other examination tools. Each probe will also incorporate a light source lead and can be formed in various degrees of deflection and sizes. The modified coupling operatively joins ends of the probe 2 and optical fiber 6 together such that light rays may be efficiently transferred therebetween, and will preferably comprise a first member 40' disposed about the end of the probe 2 and which selectively snap-fits, screw-fits, etc. into a corresponding member 40" fixed to an end of the flexible filter 6 FIG. 2 a specific example where first member 40' has a screw-fit 42 corresponding member 40' has a receiving end 44 for receiving screw-fit end 42.

According to an important aspect of the invention, the optical fiber 6 will be sufficiently long (such as 4–12 feet) and flexible that the end adjacent to the coupling 4 may be freely rotated and greatly manipulated as desired during an examination procedure, while the opposite end connected to the eyepiece 8 remains stably attached in a fixed position relative to the bands 12 and 14 on an examiner's head. A length of the fiber 6 less than 4 feet may be insufficient, especially for tall examiners, while any length greater than 12 feet is normally unnecessary even for very tall examiners, and would increase the cost of the extension. Through such feature the examiner is free to greatly manipulate the body probe 2 using both hands and to otherwise position his/her head and torso in any desired, comfortable position without regard to the probe 2. The optical fiber 6 is sheathed in an appropriate flexible, light-blocking material, and the quality of an image as directly viewed by an examiner through the eyepiece 8 is optimum.

Referring to FIGS. 3 and 4, the bands 12 and 14 are preferably formed of a lightweight rigid material such as plastic or aluminum, and are preferably covered with a soft fabric material (not shown) for comfort. The adjustment means 17 preferably includes a plurality of adjustment pins 17' about which each of the bands 12 and 14 may be selectively adjusted listed in size, i.e., the band 14 may be adjusted by being slid along slots 21 which snugly engage the pins 17' and the band 12 may be adjusted in size by having an overlapping portion 22 thereof also slid along the pins 17' via a slot 22' which also snugly engages the 17'. Further, the band 14 may be rotated relative to the band 12 about the pins 17'. The clips 16 may be of any appropriate structure for selectively securing the optical fiber 6 therein, but as shown in FIGS. 3 and 4 will preferably comprise substantially U-shaped members into which the optical fiber sheath may be selectively snap-fitted. Other headband structures, adjustable and nonadjustable, could be used according to the invention, such as the headband shown in U.S. Pat. No. 3,830,230.

The support arm 18 is, also, preferably constructed of a lightweight rigid material such as aluminum or plastic, and his one end fixed to the band 12 at a position where it will be located substantially forwardly and above a user's eye (for example the user's right eye as shown in FIG. 3) when the band 14 is disposed relative to the user's ear, as shown in FIG. 4. The opposite end of the arm 18 is formed into a substantially hollow socket 18', while one end of the eyepiece mount 19 has a ball 20 formed thereon. The ball 20 is fixed within the socket 18' and together these components constitute a universal type pivot joint permitting some movement in back-and-forward, side-to-side and up-and-down directions such that the mount 19 may be rotated three-dimensionally relative to the support arm 18 and the user may achieve a most desired orientation of the eyepiece 8.

Still referring to FIGS. 3 and 4, the eyepiece mount 19 also has an eyepiece mounting frame 23 which is formed integrally with the ball 20 and a connection shaft therebetween. Again, the mounting frame 23 and ball 20 may be constructed of a rigid, lightweight material such as aluminum or plastic. The mounting frame 23 has an opening 23' defined therethrough which is slightly smaller than the large end of the eyepiece 8 so that the eyepiece 8 may be snugly fitted thereto, and a plurality of clips 24 provided on the outer face of the mounting frame around the opening 23' and which may be selectively moved into engagement with the eyepiece 8 for securing the eyepiece in snug engagement within the opening 23'. Most preferably, the clips 24 are spring clips which normally will bias the eyepiece toward the mounting frame 23, but which can be easily disengaged from the eyepiece. Optionally, a pair of the eyepiece mounts 19 and support arms 18 may be provided on the band 12 and which are aligned with a user's right eye and left eye, respectively. With such option, the eyepiece 8 may be mounted to either of the mounts 23 for being operatively disposed in front of an examiner's right or left eye, as desired, while the other eyepiece mount 23 may be pivoted upwardly out of view of the examiner.

Figure 7:
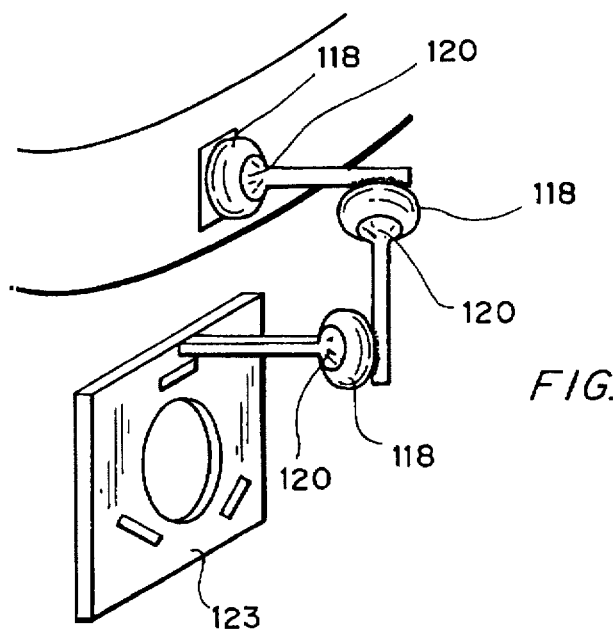
FIG. 7 is a perspective view of a modified universal joint of the positioning portion from that shown in FIGS. 3 and 4.

Referring to FIG. 7, there is shown al modification of the pivoting support structure for a mounting frame 123 for the eyepiece of the flexible endoscopic apparatus according to the invention. The modified support structure includes a plurality (three) of universal type pivot joints instead of a single joint as shown in FIGS. 3 and 4. Each of the pivot joints preferably comprises a ball 120 and socket 118 similar to the pivot joint in FIGS. 3 and 4, and collectively the plurality of pivot joints in the modified support structure permits the mounting frame 123 to be more accurately positioned relative to an examiner's eye. Further, although the mounting frame 23 or 123 depicted in FIGS. 3, 4, and 7 is preferred, other appropriate eyepiece support members may be used according to the invention, such as the eyepiece mount disclosed in U.S. Pat. No. 4,256,561.

During use of the flexible endoscopic apparatus according to the invention, the eyepiece 8 and remote end of the optical fiber 6 will be secured to the mounting frame 23 extending from the band 12, the bands 12 and 14 will be adjustably fitted over the examiner's head and the eyepiece mount 19 will be rotatably adjusted to a desired position in front of the examiner's viewing eye; the examiner will (if necessary) attach an appropriate light source to the coupling 4 or probe 2, the examiner will arrange himself/herself comfortably in a desired position (such as sitting upright) adjacent the patient to be examined, focus the probed image with adjustment knob 7, and will conduct a probing examination through significant manipulations of the probe 2 using his/her hands, while otherwise maintaining his/her head and torso in the desired, comfortable position and directly viewing the probed image through the eyepiece. Due to the fact that both of the examiner's hands are free to manipulate the body probe 2, whereas with a conventional endoscope the examiner normally is required to use one hand for holding the eyepiece 8 in a steady position against the examiner's viewing eye, and because the examiner's head and torso are positioned comfortably during an examination using the apparatus according to the invention rather than a conventional endoscopic apparatus, the examiner is permitted to conduct a more thorough, dexterous and comfortable examination.

In body examining procedures such as endoscopy, colonoscopy, and cystoscopy, it is desirable to use a flexible or rigid probe according to the nature of the procedure and the preference of the operator. The apparatus according to the present invention may be used for all such procedures. Additionally, the probe 2 may be formed in various degrees of deflection for use in standard endoscopic sheaths, and furthermore may be formed in various sizes for use in applications such as ureteroscopy and pediatric cystoscopy, so sized as to fit into appropriate sized sheaths for these applications.

Figure 5:
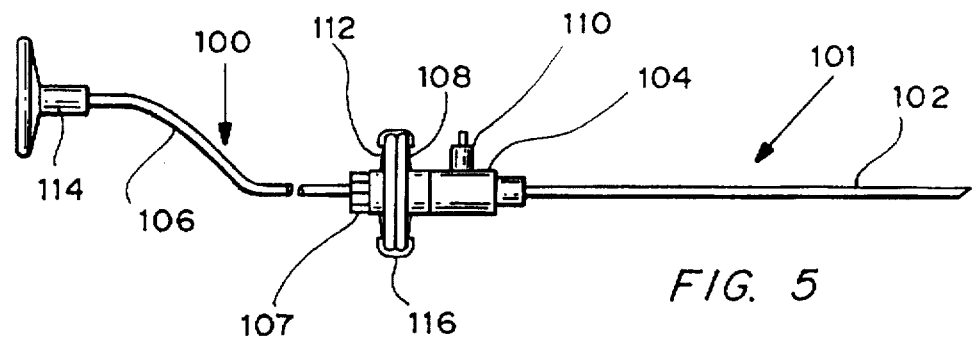
FIG. 5 is a side view of a conventional endoscope connected to a flexible extension according to a second embodiment of the invention.

Referring to FIG. 5, there is shown a second preferred embodiment of the invention, or more precisely, a variation of the flexible light-transmitting portion of the first embodiment of the invention as shown in FIG. 1. According to this embodiment/variation, a flexible extension 100 is provided together with a coupling means 116 for connecting the extension to a conventional endoscope indicated at 101. The conventional endoscope 101 includes a body cavity probe 102, an eyepiece 108, a coupling 104 for coupling the probe to a light source and other attachments, including a light source fitting 110. The probe 102 and light source fitting 110 may be the same as the probe 2 and light source fitting 10 of the first embodiment, while the coupling 104 and eyepiece 108 are substantially the same as the coupling 4 and eyepiece 8 of the first embodiment except that they are coupled together rather than to opposite ends of an optical fiber.

Still referring to FIG. 5, the flexible viewing extension 100 includes an elongate, flexible optical fiber 106 and a pair of eyepieces 112 and 114 connected to opposite ends thereof. The optical fiber 106 is preferable 4–12 feet in length and sheathed in a flexible sheath similar to the optical fiber 6 of the first embodiment. The eyepiece 112 preferably has a focus adjustment knob 107 disposed adjacent thereto, while the eyepiece 114 preferably has substantially the same construction as the eyepiece 8 shown in FIGS. 3 and 4. The coupling means 116 can be simply comprised of one or more retainers formed of spring steel, plastic or other appropriate material for maintaining the eyepieces 108 and 112 in a fixed position relative to each other. Preferably, the coupling means 116 permits the eyepieces 108, 112 or 114 to be rotated relative to each other. Alternatively, the coupling means 116 may have a more substantive structure such as that disclosed in U.S. Pat. No. 5,156,141, and/or the coupling means may be constructed integrally with the eyepiece 112.

Use of the flexible endoscopic extension according to the second embodiment is substantially the same as use of the first embodiment of the invention as described above, except that the procedure also includes an additional step of connecting the flexible extension 100 to the conventional endoscope 101 using the coupling means 116. The advantages achieved using the second embodiment of the invention include all of those discussed above in relation to the first embodiment, plus an additional advantage that the flexible extension may be used with substantially any conventional endoscope or other similar body probing scope so that the users need not discard their conventional endoscopes, but may instead use their conventional endoscopes with the flexible extension according to the invention.

Figure 6:
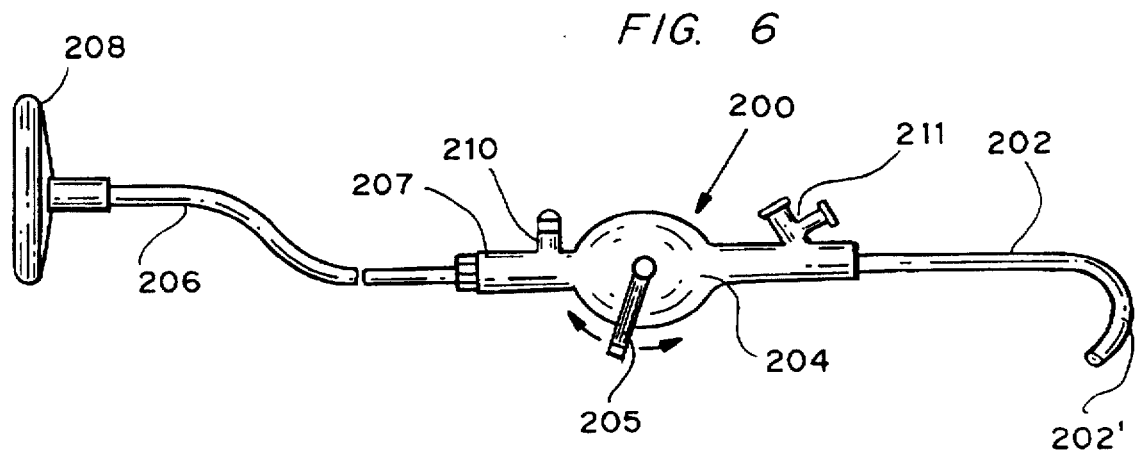
FIG. 6 is a side elevational view of a flexible endoscopic apparatus according to a third preferred embodiment of the invention.

Referring to FIG. 6, there is shown a flexible endoscopic apparatus 200 according to a third preferred embodiment of the invention. The apparatus includes a flexible probe or telescope 202, a handle portion 204 with an attachment 210 for a high intensity light source and another attachment 211 for a water source, a catheter, etc., a pivoting lever 205 which may be pivoted relative to the handle 204 for flexing a tip portion 202' of the probe 202 upwardly and downwardly in a conventional manner, a focus adjustment knob 207, an elongate, flexible optical fiber 206, and an eyepiece 208 disposed at a remote end of the fiber 206. The flexible probe 202 includes lenses therein for transmitting light from a light source to the probe tip 202' and from the tip to the optical fiber 206, as with the first and second embodiments, although the lenses of the flexible probe are preferably flexible optical fiber bundles, and the fiber bundle transmitting reflected light back to the optical fiber 206 may be formed integrally with the fiber 206. Use of the apparatus 200 according to the third embodiment is the same as that of the apparatus 1 according to the first embodiment except that the probe 202 is flexible and the tip portion 202' can be manipulated up and down with the lever 205.

Although there have been described what are at present considered to be the preferred embodiments of the invention, it will be understood by persons skilled in the art that the invention may be embodied in other specific forms without departing from the spirit or important characteristics of the invention. The scope of the invention is indicated by the appended claims rather than by the foregoing description.

We claim:

1. An attachment which can be coupled to an endoscope having an eyepiece, comprising:
    a flexible extension capable of extending an optical output of an endoscope eyepiece to a remote location;
    a receiving lens positioned at one end of the flexible extension capable of receiving light output from an endoscope eyepiece;
    a coupling device capable of attaching the one end of the flexible extension to an endoscope eyepiece which includes a retainer for securing the receiving lens and the eyepiece together in an optically transmissive relationship wherein the coupling device permits the endoscopic eyepiece to rotate relative to the receiving lens when the attachment is attached to an endoscope eyepiece, and
    means for stably positioning a remote end of the flexible extension in front of an eye of a person at the remote location.

2. An attachment according to claim 1, wherein the flexible extension further includes an elongate optical fiber having one end connected to the receiving lens, and an output lens connected to a remote end of the optical fiber.

3. An attachment according to claim 2, wherein the optical fiber is sufficiently long and flexible to permit the receiving lens to be freely rotated and manipulated while the output lens is stably positioned by the positioning means.

4. An attachment according to claim 2, wherein the flexible extension further includes a flexible, light-blocking sheath enclosing the optical fiber.

5. An attachment according to claim 2, wherein the positioning means includes a support band capable of being disposed on a user's head, clamps connected to the support band capable of selectively clamping the output lens thereto, and means for securing an intermediate portion of the optical fiber to upper and rear portions of the support band.

6. An attachment according to claim 5, wherein the clamp includes an eyepiece mount with an opening defined therethrough for receiving the output lens, and retaining means for selectively securing the output lens to the mount.

7. An attachment according to claim 6, wherein the retaining means includes a plurality of spring clips connected to the eyepiece mount.

8. An attachment according to claim 1, wherein the flexible extension includes an elongate optical fiber and an eyepiece connected to a remote end of the optical fiber.

9. An attachment according to claim 8, wherein the optical fiber is sufficiently long and flexible that the one end of the optical fiber may be freely rotated and manipulated while the remote end of the optical fiber is stably positioned by the positioning means.

10. An attachment according to claim 1, wherein the flexible extension has a length of between four and twelve feet.

11. The attachment of claim 1 wherein the coupling device comprises spring clips.

12. A flexible endoscopic apparatus, comprising:
    a light-transmissive probe for being inserted within a body cavity, the probe including a first lens for transmitting light from a light source to one end of the probe and a second lens for receiving reflected light in one end and transmitting the reflected light to an opposite end of the probe;
    an elongate, flexible optical fiber having one end coupled to a receiving lens at the opposite end of the probe for receiving the reflected light from the opposite end of the probe;
    a coupling device positioned between the probe and the elongate optical fiber capable of coupling the probe to a high intensity light source;
    an eyepiece and output lens connected to another end of the optical fiber;
    means for positioning the eyepiece in front of an eye of a user;

wherein the optical fiber is sufficiently long and flexible that one end of the fiber may be freely rotated and manipulated while the eyepiece is maintained in the desired position by the positioning means.

wherein the receiving probe lens and the flexible optical fiber are formed as an integral, unitary member.

13. An endoscopic apparatus according to claim 12, wherein the first and second probe lenses are formed of rigid material.

14. An endoscopic apparatus according to claim 12, wherein the first and second probe lenses are formed of flexible material.

15. An endoscopic apparatus according to claim 12, wherein the flexible optical fiber is between four and twelve feet long.

16. A direct visualization flexible extension capable of being coupled to an endoscope, comprising:

a flexible extension capable of extending an optical output of an endoscope to a remote location, the flexible extension including an elongate optical fiber having one end connected to the receiving lens of an endoscope and an eyepiece connected to an opposite end of the optical fiber;

a coupling device capable of joining the flexible extension to an endoscope wherein the coupling device permits an endoscopic eyepiece to rotate relative to the receiving lens when the attachment is attached to an endoscope eyepiece; and means for stably positioning the eyepiece in front of an eye of a person for direct visualization at the remote location;

wherein the optical fiber is sufficiently long and flexible to permit the one end to be freely rotated and manipulated while the eyepiece is stably positioned by the positioning means;

and wherein the flexible extension means is unencumbered with a device for providing light to an endoscope.

17. An extension according to claim 16, wherein the coupling device is fixed to the one end of the flexible extension and is adapted to selectively receive an endoscope.

18. The extension of claim 17 wherein the coupling device provides a fit between the flexible extension and the endoscope that is selected from the group consisting of a snap-fit and a screw-fit.

19. An extension according to claim 16, wherein the optical fiber is between four and twelve feet long.

20. A method of using an attachment which can be coupled to an endoscope having an eyepiece, comprising:

providing an attachment for an endoscope comprising
a flexible extension capable of extending an optical output of an endoscope eyepiece to a remote location,
a receiving lens positioned at one end of the flexible extension capable of receiving light output from an endoscope eyepiece,
a coupling device capable of retaining the attachment at the one end of the flexible extension to an endoscope eyepiece wherein the coupling device permits the endoscopic eyepiece to rotate relative to the receiving lens when the attachment is attached to an endoscopic eyepiece, and means for stably positioning a remote end of the flexible extension in front of an eye of a person at the remote location;
providing an endoscope having an eyepiece;

attaching the attachment to the eyepiece with the coupling device;

stably positioning the remote end of the flexible extension in front of the eye of the person; and viewing the optical output of the endoscope through the remote end of the flexible extension.

21. A method of using a flexible endoscopic apparatus, comprising:

providing a flexible endoscopic apparatus comprising
a light-transmissive probe for being inserted within a body cavity, the probe including a first lens for transmitting light from a light source to one end of the probe and a second lens for receiving reflected light in one end and transmitting the reflected light to an opposite end of the probe, a flexible optical fiber having one end coupled to the receiving end at the opposite end of the probe for receiving the reflected light from the opposite end of the probe,
a coupling device positioned between the probe and the elongate capable of coupling the probe to a high intensity light source,
an eyepiece and output lens connected to another end of the optical fiber,
means for positioning the eyepiece in front of an eye of a user, the optical fiber is sufficiently long and flexible that the one end of the fiber may be freely rotated and manipulated while the eyepiece is maintained in the desired position by the positioning means;

positioning the eyepiece in front of the eye of the user;

coupling a high intensity light source to the probe at the coupling device; and viewing the eyepiece.

22. A method for using an endoscope comprising coupling to the endoscope a direct visualization extension capable of extending an optical output of an endoscope to a remote location, the flexible extension including an elongate optical fiber having one end connected to the receiving lens of an endoscope and an eyepiece connected to an opposite end of the optical fiber;

a coupling device capable of joining the flexible extension to an endoscope wherein the coupling device permits an endoscopic eyepiece to rotate relative to the receiving lens when the attachment is attached to an endoscope eyepiece; and means for stably positioning the eyepiece in front of an eye of a person for direct visualization at the remote location;

wherein the optical fiber is sufficiently long and flexible to permit the one end to be freely rotated and manipulated while the eyepiece is stably positioned by the positioning means, and wherein the direct visualization extension is unencumbered with a device for providing light to an endoscope;

providing an endoscope having an independent light source;

attaching the extension to the endoscope;

positioning the eyepiece in front of the eye of the person; and viewing the optical output of the endoscope through the eyepiece.

* * * * *